(12) United States Patent
Takai et al.

(10) Patent No.: US 6,530,091 B2
(45) Date of Patent: Mar. 11, 2003

(54) MEANS FOR ATTACHMENT OF ABSORBENT ARTICLE FOR BODY EXUDATES TO UNDERGARMENT

(75) Inventors: Hisashi Takai; Miou Suzuki; Kaori Yamauchi; Maki Watanabe; Sachiyo Suzuki, all of Kagawa-ken (JP)

(73) Assignee: Uni-Charm Corporation (JP)

( * ) Notice: Subject to any disclaimer, the term of this patent is extended or adjusted under 35 U.S.C. 154(b) by 17 days.

(21) Appl. No.: 10/013,900

(22) Filed: Oct. 30, 2001

(65) Prior Publication Data

US 2002/0050001 A1 May 2, 2002

(30) Foreign Application Priority Data

Oct. 31, 2000 (JP) .................................... 2000-333444
Oct. 25, 2001 (JP) .................................... 2001-328216

(51) Int. Cl.$^7$ ............................ A61F 13/15; A49B 9/00
(52) U.S. Cl. ........................ 2/406; 604/393; 604/397; 604/402
(58) Field of Search ........................ 2/406, 408, 400; 604/385.03, 386, 387, 389–402

(56) References Cited

U.S. PATENT DOCUMENTS

| 5,264,268 | A | | 11/1993 | Luceri et al. | |
|---|---|---|---|---|---|
| 5,429,633 | A | * | 7/1995 | Davis et al. | 604/387 |
| 5,478,335 | A | | 12/1995 | Colbert | |
| 5,650,223 | A | * | 7/1997 | Weinberger et al. | 604/385.1 |
| 5,681,304 | A | * | 10/1997 | Van Iten | 604/387 |
| 5,683,375 | A | * | 11/1997 | Osborn, III et al. | 604/385.2 |
| 5,711,034 | A | * | 1/1998 | Cillik | 2/406 |

FOREIGN PATENT DOCUMENTS

WO    WO 00/13640    3/2000

OTHER PUBLICATIONS

Copy of European Search Report dated Feb. 25, 2002.

* cited by examiner

Primary Examiner—Gloria M. Hale
(74) Attorney, Agent, or Firm—Baker & Daniels

(57) ABSTRACT

Support for attaching an absorbent article such as a sanitary napkin to an undergarment and disposed between a sanitary napkin and an inner surface of a crotch region of the undergarment. The support is formed by a first sheet and a second sheet overlying the first sheet. The first sheet 6 is elastically flexible and stretchable in its longitudinal direction and the second sheet has its longitudinally opposite end portions bonded to longitudinally opposite end portions of the first sheet and elastically stretchable at least in the longitudinal direction. The inner surface of the second sheet is formed so that the outer surface of the napkin may be fixed thereon.

7 Claims, 7 Drawing Sheets

MEANS FOR ATTACHMENT OF ABSORBENT ARTICLE FOR BODY EXUDATES TO UNDERGARMENT

BACKGROUND OF THE INVENTION

This invention relates to a means for attachment of an absorbent article such as a sanitary napkin and a pad used by a person suffering from incontinence to an undergarment such as a panty.

It is well known to use a sanitary napkin in a state almost fixed to an undergarment such as a panty or pants worn by its user. To this end, it is also well known to coat a surface of the sanitary napkin facing the undergarment with pressure-sensitive adhesive. The surface may be a lower surface of the sanitary napkin's basic structure or lower surfaces of paired wings extending laterally from the basic structure.

The conventional sanitary napkin which is as described above practically fixed to the undergarment can not reliably adapt about to the movement of the wearer's body. The sanitary napkin would be spaced from the wearer's body and cause leakage of menstrual discharge if the sanitary napkin can not adapt to the movement of the wearer's body.

SUMMARY OF THE INVENTION

It is an object of this invention to facilitate an absorbent article for body exudates such as a sanitary napkin and a pad used by a person suffering from incontinence to adapt to the movement of the wearer's body reliably.

According to this invention, there is provided a means for attachment of an absorbent article to an inner surface of a crotch region of an undergarment worn by the wearer. The absorbent article has an inner surface facing the wearer's skin, an outer surface facing the undergarment worn by the wearer, a longitudinal direction corresponding to a back and forth direction of the undergarment and a transverse direction being orthogonal to the longitudinal direction. The means is disposed between the outer surface of the absorbent article and the inner surface of the undergarment's crotch region to attach the absorbent article to the inner surface of the crotch region.

The means comprises a first sheet being relatively long in the longitudinal direction and a second sheet overlying the first sheet as viewed in a vertical direction of the undergarment. The first sheet has an inner surface facing the second sheet and an outer surface facing the crotch region's inner surface, the first sheet being elastically flexible and stretchable in the longitudinal direction so as to expand along the crotch region's inner surface. The second sheet has an inner surface facing the absorbent article and an outer surface facing the first sheet, the second sheet being elastically flexible and stretchable at least in the longitudinal direction. The inner surface of the first sheet is formed with a means by which the first sheet is detachably fixed to the crotch region's inner surface and the inner surface of the second sheet is formed with a means by which the outer surface of the absorbent article can be fixed to this inner surface of the second sheet.

DETAILED DESCRIPTION OF THE PREFERRED EMBODIMENTS

Details of a means according to this invention for fixing a sanitary napkin as a typical example of the absorbent article to an undergarment will be more fully understood from the description with reference to the accompanying drawings.

Figure 1:
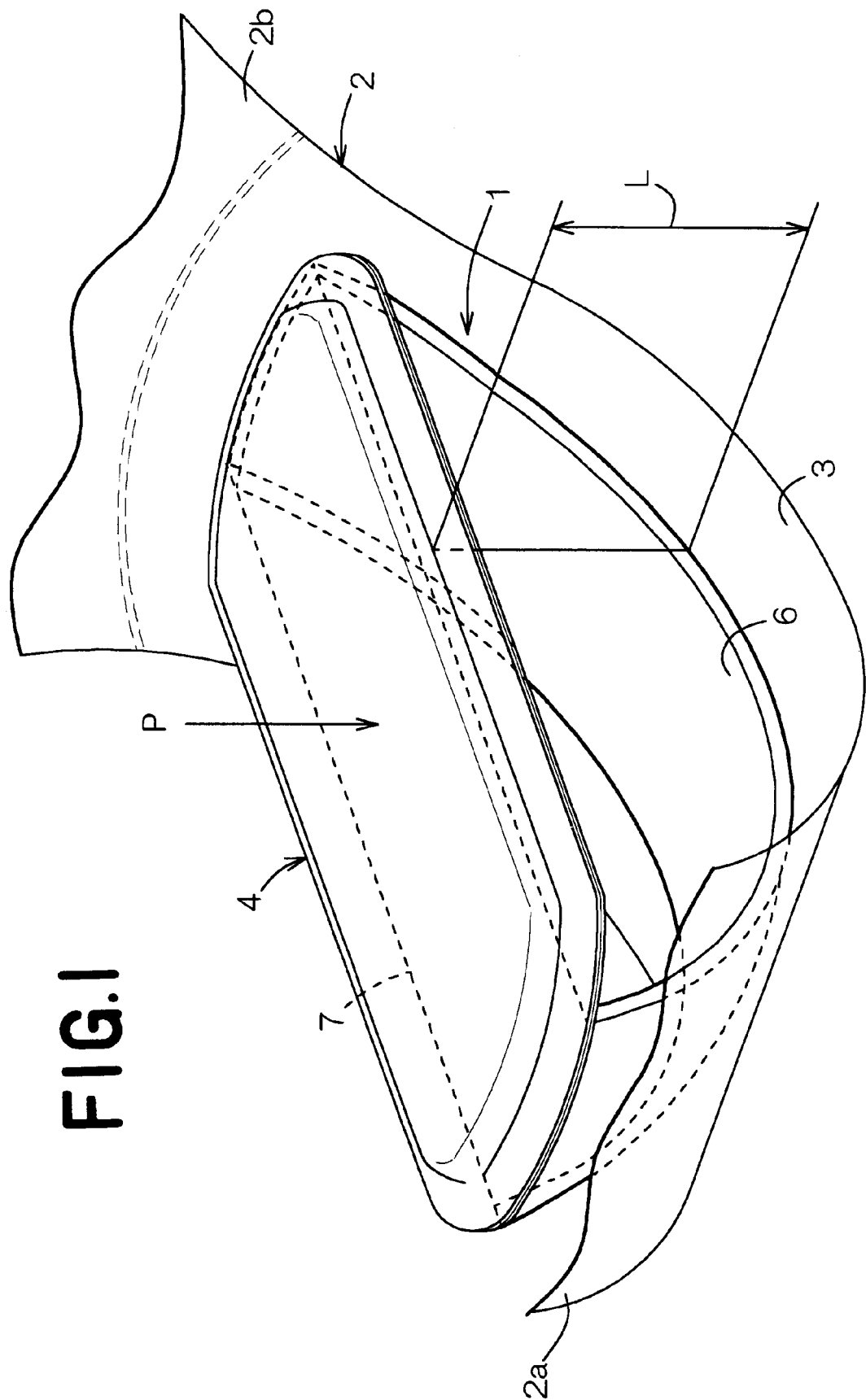
FIG. 1 is a perspective view showing a supporting means during its actual use.

FIG. 1 is a perspective view showing a napkin supporting means 1 as one embodiment of the means which has been attached to a crotch region 3 of an undergarment 2 such as a panty worn by a wearer of the undergarment 2. The crotch region 3 extends in the longitudinal direction between a front region 2a and a rear region 2b of the undergarment 2. The supporting means 1 and a sanitary napkin 4 supported thereby have a longitudinal direction and a transverse direction and are shaped to be relatively long in the longitudinal direction. The longitudinal direction of the supporting means 1 and the sanitary napkin 4 coincides with the longitudinal direction of the crotch region 3. The supporting means 1 has a bottom sheet 6 and a top sheet 7 wherein the bottom sheet 6 is curved in the longitudinal direction along the inner surface of the crotch region 3. The topsheet 7 extends in a flat out state between longitudinally opposite ends of the bottom sheet to support the sanitary napkin 4 from below as viewed in FIG. 1 and facilitates the napkin 4 to be maintained in close contact with the user's skin.

Figure 2:
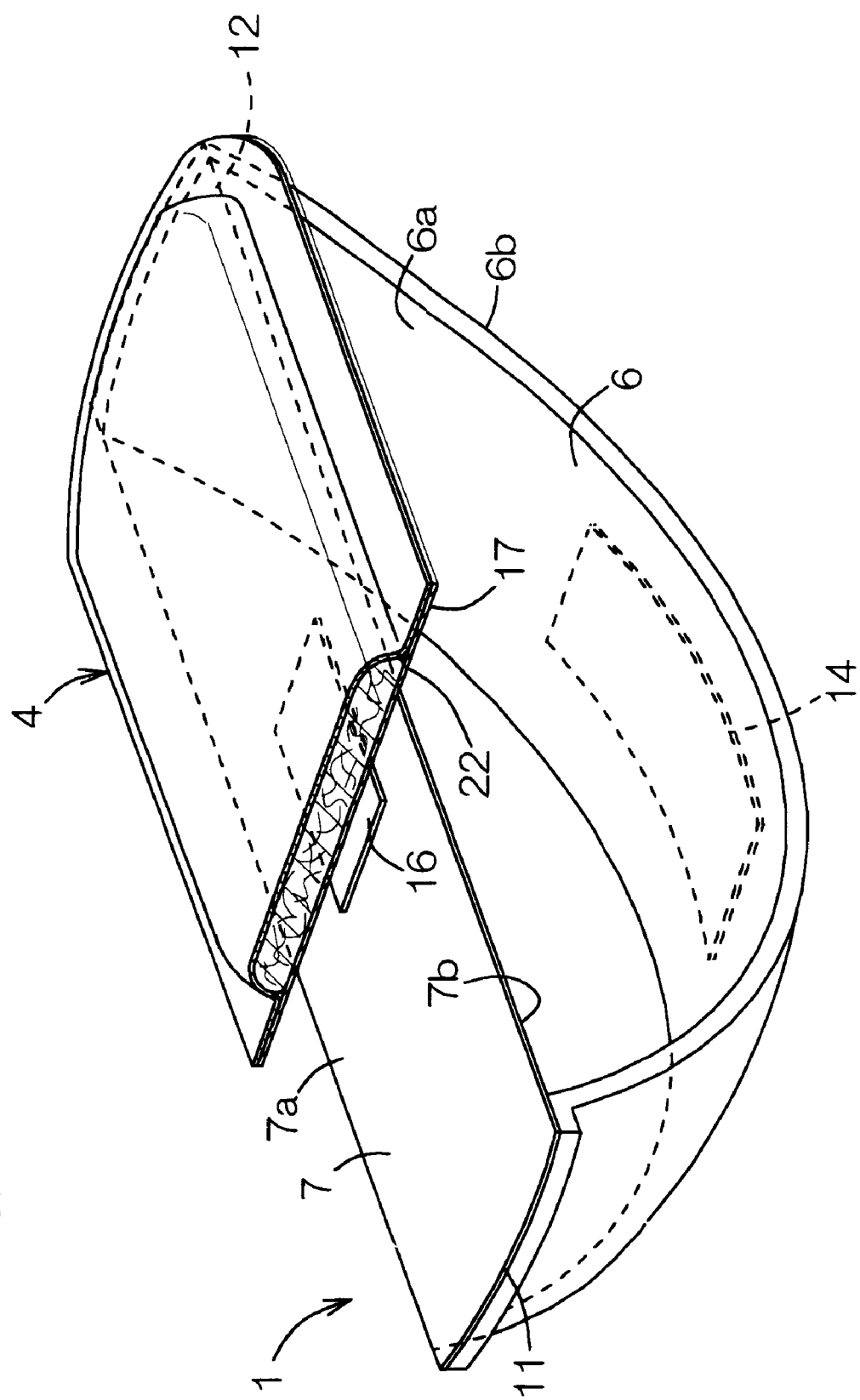
FIG. 2 is a partially cutaway perspective view similar to that in FIG. 1.

FIG. 2 is a perspective view showing the supporting means 1 together with the sanitary napkin 4 in which the sanitary napkin 4 is shown as partially cutaway. The bottom sheet 6 of the supporting means 1 has an inner surface 6a facing the top sheet 7 and an outer surface 6b facing the crotch region 3 of the undergarment 2. The bottom sheet 6 may be formed by a sheet adapted to be elastically deformed from a state which is flat in the longitudinal direction to a state which is curved in the longitudinal direction or a sheet adapted to be elastically deformed from a state which is curved as shown to a state which is flattened. The embodiment shown in FIG. 1 adopts the former, i.e., an initially flat sheet as the bottom sheet 6. These sheets may have a thickness in the order of about 0.2–2 mm and a material for them may be selected from a group including a thermoplastic sheet, a thermoplastic foamed sheet, a sheet of elastomer such as synthetic rubber, a foamed elastomer sheet, these sheets molded in a curved shape and injection molded into an article of thermoplastic material. In its flat state, dimension of such bottom sheet 6 may be determined in its length and width depending on the sizes of the undergarment 2 with which the supporting means 1 is to be used and generally may have a longitudinal dimension of about 100–300 mm and a transverse dimension of about 10–70 mm, wherein the transverse dimension is preferably smaller than the width of the sanitary napkin 4. This bottom sheet 6 has its flexural modulus adjusted in its longitudinal and transverse directions so that a smooth movement of the wearer s body as well as the undergarment 2 may not be obstructed by the bottom sheet 6. The bottom sheet 6 is substantially fixed to the inner surface of the undergarment inner surface in a first adhesive zone 14 formed by pressure-sensitive adhesive applied on its outer surface 6b (See FIG. 1).

The top sheet 7 as another component of the supporting means 1 comprises a sheet adapted to be elastically stretchable in its longitudinal and transverse directions, at least in its longitudinal direction and having an inner surface 7a facing the napkin 4 and an outer surface 7b facing the bottom sheet 6. Such top sheet 7 may be made of an elastically stretchable film, a net, a nonwoven fabric or a woven fabric and fixed to longitudinally opposite end portions 11, 12 of the bottom sheet 6 by appropriate means such as adhesion, welding or stitching. Such top sheet 7 is fixed to the bottom sheet 6 with or without longitudinal tension, preferably with the longitudinal tension so that the outer surface 6b of the bottom sheet 6 may form a convex curve as seen in FIG. 1. Preferably, contraction of the top sheet 7 causes the bottom sheet 6 to be curved with the maximum distance L (See FIG. 1) of about 10–70 mm from the top sheet 7.

The supporting means 1 of the above described arrangement is peelably fixed to the inner surface of the shorts' crotch region 3 in the first adhesive zone 14 formed on the outer surface 6b of the bottom sheet 6 in its longitudinally and transversely middle region. On the inner surface 7a of the top sheet 7 facing the outer surface 17 of the sanitary napkin 4 is formed in its longitudinally and transversely middle region a second adhesive zone 16 by applying a pressure-sensitive adhesive thereon. This second adhesive zone 16 allows the outer surface 17 of the sanitary napkin 4 to be peelably or non-peelably fixed in its longitudinally and transversely middle region to the supporting means 1. In this manner, the sanitary napkin 4 is bonded only in its central region to the top sheet 7.

Figure 3:
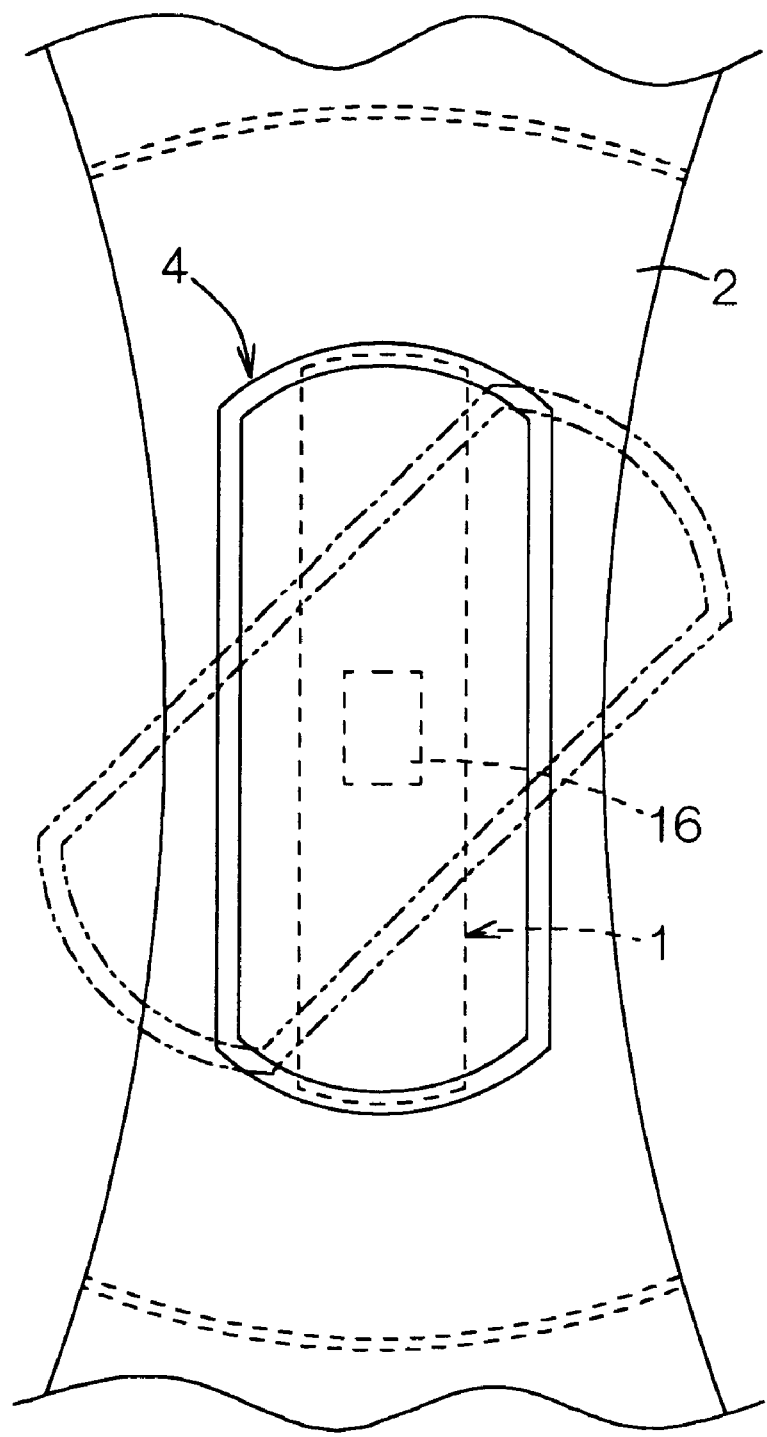
FIG. 3 is a plan view showing the supporting means together with a sanitary napkin.

FIG. 3 is a plan view showing the sanitary napkin 4 in a state of FIG. 1, in which the supporting means 1 positioned beueath the sanitary napkin 4 are indicated by broken lines. As will be apparent from the foregoing description, the sanitary napkin 4 is fixed only in the central region of its outer surface 17 to the second adhesive zone 16 formed in the central region of the elastically stretchable top sheet 7. Thus the sanitary napkin 4 is rotatable in a clock- and counterclockwise direction, namely in a transverse direction of the undergarment 2, preferably in a clock- and counterclockwise direction by 30–60° around the second adhesive zone 16 as indicated by imaginary lines. When a body weight pressure P of the shorts' wearer is exerted upon the sanitary napkin 4 from above, the top sheet 7 is stretched so that the napkin 4 may be moved downward and come more closely in contact with the wearer's body. When the wearer's body moves back and forth relative to the undergarment 2, the sanitary napkin 4 in close contact with the wearer's body also can move back and forth together with the wearer's body since the topsheet 7 is stretchable back and forth.

In this manner, the supporting means 1 functions to maintain the sanitary napkin 4 spaced from the undergarment 2 but in close contact with the wearer's body so that the sanitary napkin 4 may well adapt to the movement of the wearer's body and thereby prevent leakage of menstrual discharge occurring between the wearer's body and the sanitary napkin 4.

Figure 4:
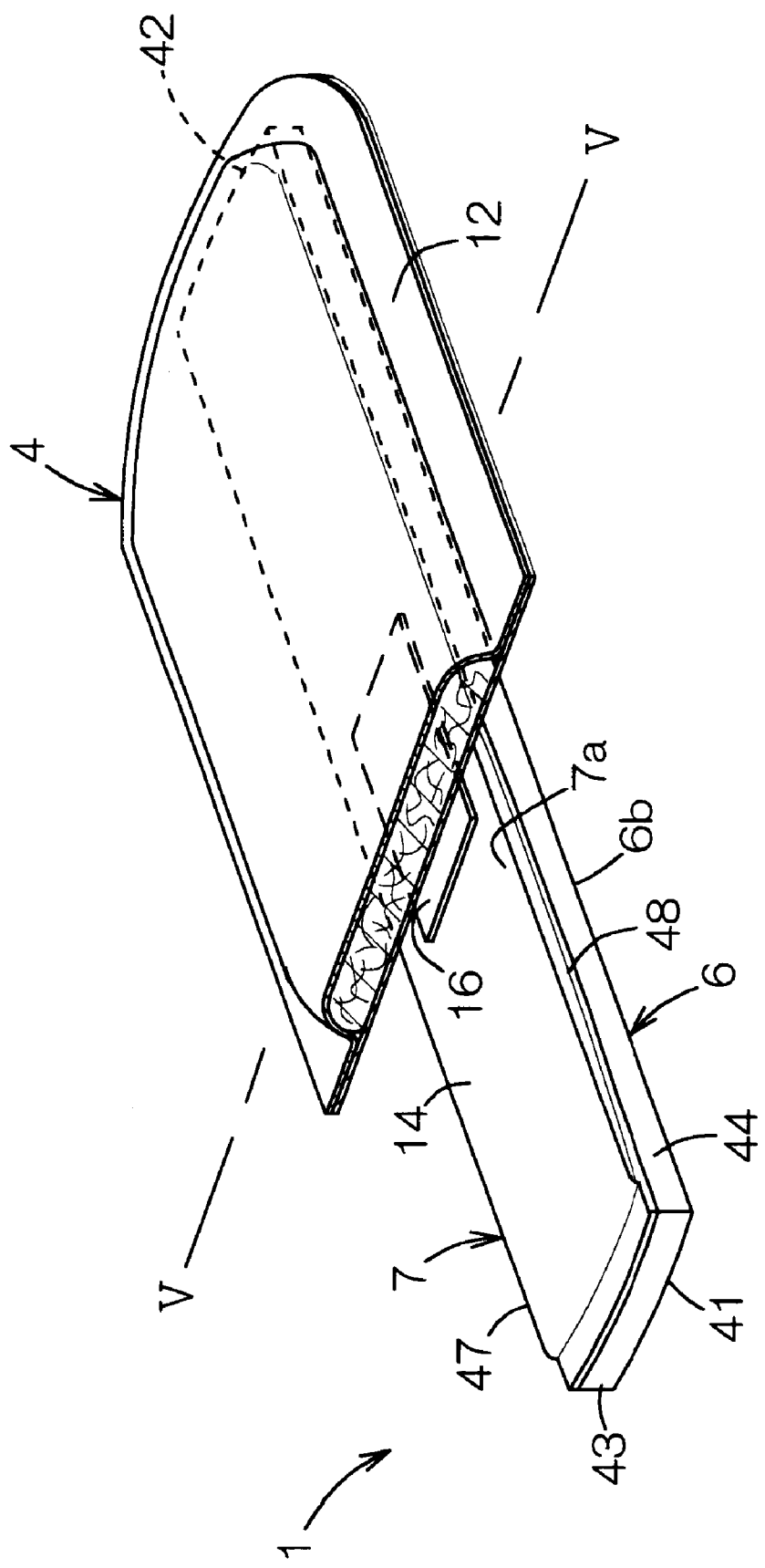
FIG. 4 is a partially cutaway perspective view showing one preferred embodiment of the supporting means.
Figure 5:
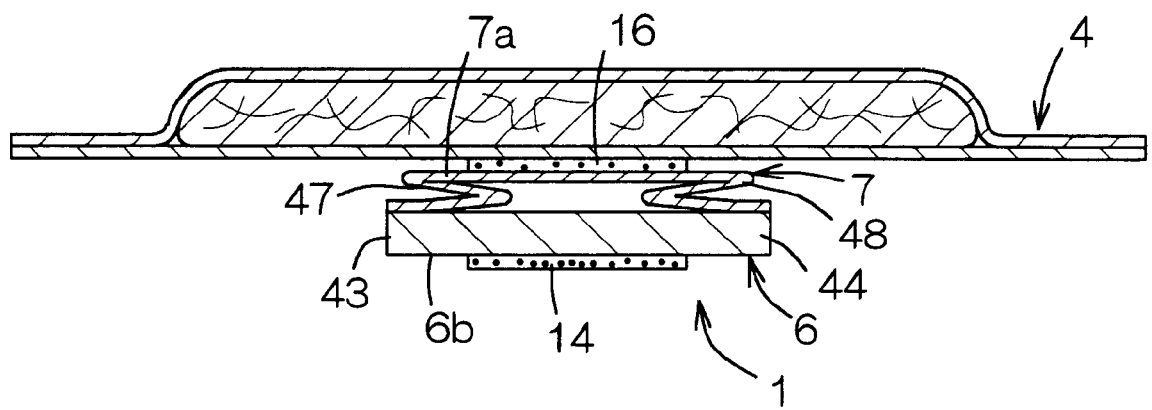
FIG. 5 is a sectional view taken along a line V—V in FIG. 4.
Figure 6:
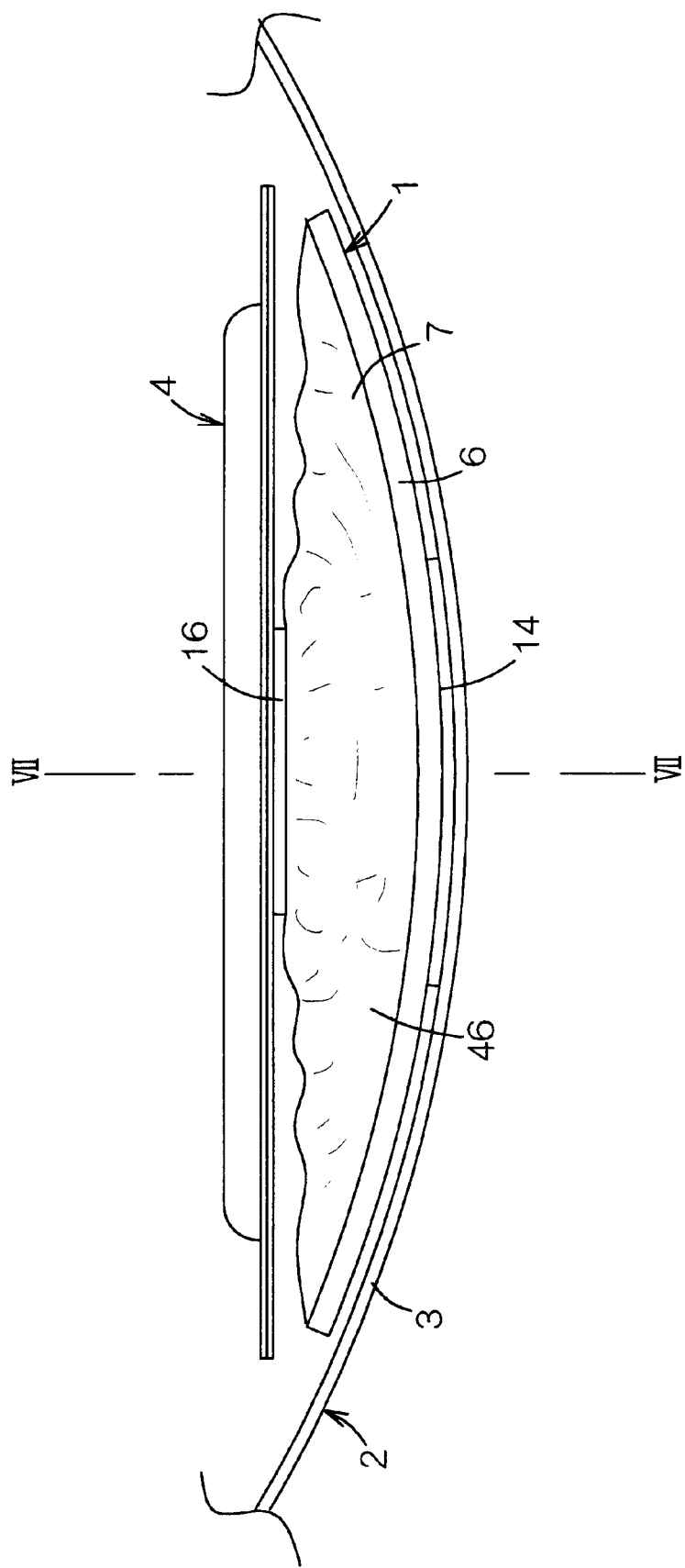
FIG. 6 is a sketch illustrating the supporting means of FIG. 4 as attached to a crotch region of an undergarment.
Figure 7:
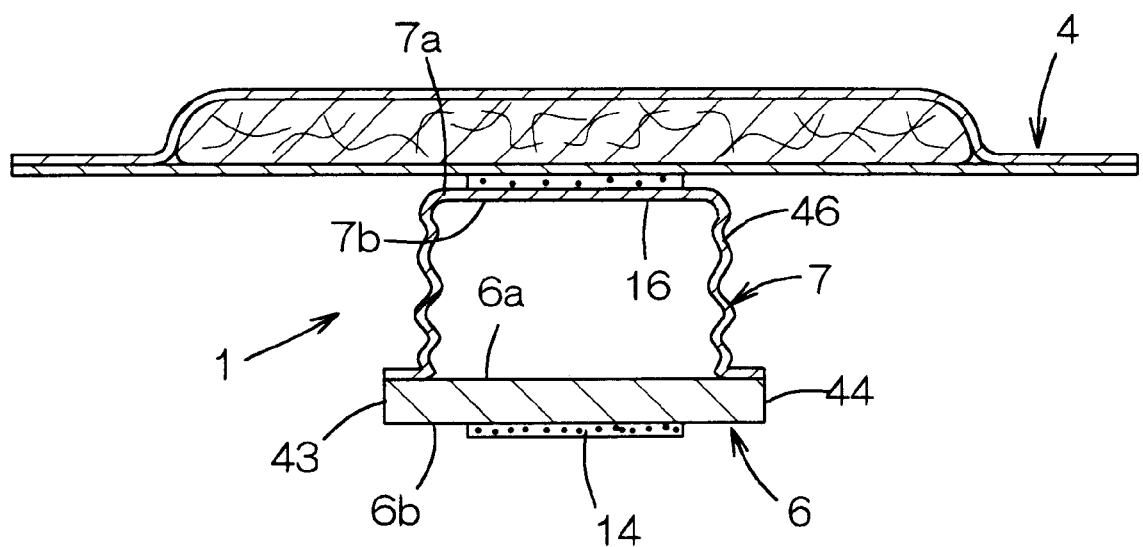
FIG. 7 is a sectional view taken along a line VII—VII in FIG. 6.

FIGS. 4, 5 and 6 show one preferred embodiment of this invention, in which FIG. 4 is a perspective view of the supporting means 1, FIG. 5 is a sectional view taken along a line V—V in FIG. 4, FIG. 6 is a side view showing the supporting means 4 of FIG. 4 laid along the inner surface of the undergarment crotch region 3 and FIG. 7 is a sectional view taken along a line VII—VII in FIG. 6. As will be apparent from FIGS. 4 and 5, the supporting means 1 according to this embodiment comprises the flat bottom sheet 6 and the top sheet 7 bonded without tension to longitudinally opposite end portions 41, 42 and transversely opposite side edge portions 43, 44 of the bottom sheet 6 and being elastically stretchable at least in the longitudinal direction. The bottom sheet 6 and top sheet 7 have a substantially same length in the longitudinal direction. The top sheet 7 has its transversely opposite side edge portions 47, 48 folded in Z-shape or an inverted Z-shape. The bottom sheet 6 has its outer surface 6b fixed to the inner surface of the undergarment crotch region 3 by means of the first adhesive zone 14 (See FIG. 6) and the sanitary napkin 4 is fixed to the inner surface 7a of the top sheet 7 by means of the second adhesive zone 16. A plurality of gathers 46 are formed on the inner surface of the curved bottom sheet 6 as seen in FIG. 6 and the sanitary napkin 4 is pushed upward by the transversely opposite side edge portions 43, 44 of the bottom sheet 6 against the shorts wearer's skin as seen in FIG. 7 as the bottom sheet 6 is curved along the undergarment's crotch region 3. This sanitary napkin 4 also is spaced from the bottom sheet 6 by the top sheet 7 and therefore can adapt to the movement of the wearer's body even though the bottom sheet 6 is practically fixed to the undergarment 2. The napkin 4 attached to the top sheet 7 can easily follow movement of the wearer's body because of the unique arrangement of the top sheet 7 such that the gathers 46 thereof as well as the top sheet 7 itself can be elastically stretched.

Within the scope of this invention, the supporting means 1 can be constructed to be reusable with the sanitary napkin 4 detachable, or disposable with the sanitary napkin 4 undetachable from the top sheet 7. According to this embodiment also, the napkin 4 attached to the top sheet 7 can easily adapt to the movement of the wearer's body since the top sheet 7 itself as well as the gathers 46 thereof can be elastically stretched.

The supporting means 1 according to this invention can be applied for various absorbent articles including the sanitary napkin 4 and a pad used by a person suffering from incontinence.

The supporting means according to this invention allows the absorbent article such as a sanitary napkin and a pad for incontinence to be attached to the undergarment worn by the wearer so that the absorbent article may be rotated in a transverse direction of the undergarment and also move up and down directions as well as back and forth directions. Such a unique arrangement enables the absorbent article to adapt to any movement of the wearer's body and thereby eliminate a leakage of body exudates such as menstrual discharge.

What is claimed is:

1. A support for attaching an absorbent article to an inner surface of a crotch region of an undergarment, said absorbent article having an inner surface facing a wearer's skin, an outer surface facing the undergarment, a longitudinal direction corresponding to front and rear portions of said undergarment and a transverse direction being orthogonal to said longitudinal direction, said support being configured to be disposed between said outer surface of the absorbent article and an inner surface of said undergarment's crotch region for attaching said absorbent article to said inner surface of said crotch region, said support comprising:

a first sheet being elongated in said longitudinal direction; and a second sheet overlying said first sheet as viewed in a vertical direction of said undergarment, said first sheet having an inner surface facing said second sheet and an outer surface facing said crotch region's inner surface, said first sheet being elastically flexible and stretchable in said longitudinal direction so as to extend along said crotch region's inner surface, said second sheet having an inner surface facing said absorbent article and an outer surface facing said first sheet, said second sheet being elastically flexible and stretchable at least in said longitudinal direction, the inner surface of said first sheet being formed with means for detachably attaching said first sheet to said crotch region's inner surface, and the inner surface of said second sheet being formed with means for attaching the outer surface of said absorbent article to the inner surface of said second sheet.

2. The support according to claim 1, wherein said second sheet is bonded under tension along said longitudinal direction to said first sheet.

3. The support according to claim 1, wherein said second sheet is bonded without tension along said longitudinal direction to said first sheet.

4. The support according to claim 1, wherein a longitudinally middle region of the outer surface of said absorbent article is attached to a longitudinally middle region of the inner surface of said second sheet.

5. The support according to claim 1 wherein said absorbent article is one of a sanitary napkin and a pad.

6. The support according to claim 1 in combination with an absorbent article.

7. The combination of claim 6, wherein absorbent article is one of a sanitary napkin and a pad.

* * * * *